(12) United States Patent
Esquivel, II

(10) Patent No.: US 7,820,101 B1
(45) Date of Patent: Oct. 26, 2010

(54) METHOD FOR SANITIZING

(76) Inventor: Rafael E. Esquivel, II, 3350 SW. 148th Ave., Suite 110, Miramar, FL (US) 33027

( * ) Notice: Subject to any disclaimer, the term of this patent is extended or adjusted under 35 U.S.C. 154(b) by 917 days.

(21) Appl. No.: 11/677,928

(22) Filed: Feb. 22, 2007

(51) Int. Cl.
*A61L 2/00* (2006.01)
*A61L 2/18* (2006.01)
*A61L 9/00* (2006.01)
*B08B 5/04* (2006.01)

(52) U.S. Cl. .............. 422/28; 422/1; 422/20; 422/292; 134/21

(58) Field of Classification Search ........ None
See application file for complete search history.

(56) References Cited

U.S. PATENT DOCUMENTS

| | | | |
|---|---|---|---|
| 5,727,732 A * | 3/1998 | Stein | 239/1 |
| 6,146,588 A * | 11/2000 | Deighton | 422/28 |
| 6,566,574 B1 * | 5/2003 | Tadros et al. | 252/186.41 |
| 6,682,606 B2 * | 1/2004 | Walker | 134/6 |
| 7,622,074 B2 * | 11/2009 | Mielnik | 422/28 |
| 2004/0028554 A1 * | 2/2004 | Hedman | 422/24 |
| 2005/0108953 A1 * | 5/2005 | Berdan et al. | 52/79.1 |
| 2005/0123436 A1 * | 6/2005 | Cumberland | 422/5 |
| 2005/0216291 A1 * | 9/2005 | Shaheen et al. | 705/1 |
| 2006/0008379 A1 * | 1/2006 | Mielnik et al. | 422/32 |
| 2007/0042139 A1 * | 2/2007 | Cooper et al. | 428/29 |
| 2007/0224080 A1 * | 9/2007 | Sparks et al. | 422/28 |
| 2008/0193650 A1 * | 8/2008 | Lyon | 427/299 |

* cited by examiner

*Primary Examiner*—Elizabeth L McKane
*Assistant Examiner*—Regina Yoo
(74) *Attorney, Agent, or Firm*—Albert Bordas, P.A.

(57) ABSTRACT

A method for sanitizing a vehicle and/or structures to proactively combat Sick Car and Sick Building Syndrome, in addition to bacteria, fungal microorganisms, viruses, mildew and mold, and any variety of organisms including *Escherichia coli*, urine, feces, HIV-1, blood, and many pathogenic and environmental microbial organisms from vehicles and/or structures.

18 Claims, No Drawings

METHOD FOR SANITIZING

BACKGROUND OF THE INVENTION

1. Field of the Invention

The present invention relates to sanitizing methods, and more particularly, to a method for sanitizing vehicles and/or structures for the elimination of bacteria, fungal microorganisms, viruses, mildew and mold.

2. Description of the Related Art

Sick Car and Sick Building Syndrome is caused by the build-up of bacteria, fungal microorganisms, viruses, mildew and mold that combine to produce unpleasant odors and potentially flu-like symptoms. This can lead to serious human health issues according to the Center for Disease Control. Similarly, build-up of bacteria, fungal microorganisms, viruses, mildew and mold may develop in general means of transportation, including, but not limited to, cars, trucks, RVs, campers, trains, aircraft, and floating vessels. Furthermore, build-up of bacteria, fungal microorganisms, viruses, mildew and mold may develop in structures including, but not limited to, residential dwellings such as houses, condos, and buildings; and commercial establishments.

Applicant is not aware of any prior art sanitizing method used on vehicles and/or structures for eliminating said bacteria, fungal microorganisms, viruses, mildew and mold.

SUMMARY OF THE INVENTION

The present invention proactively combats Sick Car and Sick Building Syndrome in addition to bacteria, fungal microorganisms, viruses, mildew and mold, and any variety of organisms including *Escherichia coli*, urine, feces, HIV-1, blood, and many pathogenic and environmental microbial organisms from vehicles and/or structures. In addition, the present invention eliminates odors caused by smoke, pet dander and body odor.

It is therefore one of the main objects of the present invention to provide a method for sanitizing vehicle and/or structures that eliminates bacteria, fungal micro-organisms, viruses, mildew and mold.

It is another object of the present invention to provide a method for sanitizing vehicle and/or structures that combats bacteria including: Pseudomani *aeruginosa* (*Pseudomonas*), *Staphylococcus aureus* (Staph), *Streptococcus pyogenes* (Strep), *Enterobacter aerogenes, Enterococcus* (*Streptococcus*) *faecalis* (Vancomycin resistant) (VREF), *Escherichia coli, Escherichia coli* 0157:H7 (*E. coli*), *Salmonella choleraesuis*, and *Staphylococcus aureus* (Staph).

It is another object of the present invention to provide a method for sanitizing vehicle and/or structures that combats viruses including: Herpes Simplex Type2 (Herpes), HIV-1 (AIDS virus), and Influenza A/Hong Kong (Influenza).

It is another object of the present invention to provide a method for sanitizing vehicle and/or structures that combats fungi including: *Trichophyton mentagrophytes*, and Athlete's foot fungus (Cause of ringworm.)

It is another object of the present invention to provide a method for sanitizing vehicle and/or structures that eliminates any variety of organisms including *Escherichia coli*, urine, feces, HIV-1, and blood.

It is another object of the present invention to provide a method for sanitizing vehicle and/or structures that eliminates pathogenic and environmental microbial organisms.

It is another object of the present invention to provide a method for sanitizing vehicle and/or structures that eliminates odors caused by smoke, pet dander and body odor.

It is yet another object of this invention to practice such a method that is inexpensive to implement and maintain while retaining its effectiveness.

Further objects of the invention will be brought out in the following part of the specification, wherein detailed description is for the purpose of fully disclosing the invention without placing limitations thereon.

DETAILED DESCRIPTION OF THE PREFERRED EMBODIMENT

The method for sanitizing vehicle and/or structures and/or structures comprises the steps of:

A) cleaning a vehicle and/or structure to be sanitized;

B) vacuuming said vehicle and/or structure with a vacuum having a hepa filter;

C) placing protective gear on a technician;

D) opening windows of said vehicle and/or structure;

E) reducing and/or eliminating all illumination means;

F) determining and noting vehicle and/or structure identification number of said vehicle and/or structure;

G) inspecting interior of said vehicle and/or structure with a high intensity long wave ultraviolet light of at least 300 nm;

H) identifying location of troubled and organic matter;

I) noting said location of identified said troubled and organic matter;

J) engaging air-conditioning system of said vehicle and/or structure;

K) engaging an atomizer;

L) applying a first chemical composition from said atomizer to said vehicle and/or structure;

M) inserting wand of said atomizer into vents of said air-conditioning system;

N) disengaging said atomizer;

O) applying a second chemical composition to all non-porous surfaces of said vehicle and/or structure;

P) wiping said second chemical composition on all non-porous surfaces of said vehicle and/or structure;

Q) re-inspecting said interior with said high intensity long wave ultraviolet light to identify said troubled and organic matter at said location and going to step K) if said troubled and organic matter is still detected;

R) certifying in written form that said vehicle and/or structure is decontaminated;

S) placing information in said vehicle and/or structure advising of next certification due; and T) drying said vehicle and/or structure for a predetermined time period.

In step A) of the method, cleaning a vehicle and/or structure to be sanitized; a certified service technician may clean the exterior of the vehicle and/or structure if desired.

As an example, for vehicles, including, but not limited to cars, trucks, RVs, campers, trains, aircraft, and floating vessels, a predetermined amount of water in a gentle stream to avoid scratches may be used. Excessive water pressure will cause dirt to grind at a vehicle surface. In the preferred embodiment, the certified service technician allows the water to flow freely out of a hose without the benefit of a nozzle. The certified service technician uses a detergent designed specifically for vehicle washing. The certified service technician starts washing the rooftop of the vehicle, and then proceeds to the vehicle's other sections including the front fender, doors, rear fender and so on, rinsing thoroughly in between. After washing, the certified service technician rinses the entire vehicle to ensure that all detergent is removed from the vehicle, especially from the vehicle's nooks, crannies and crevices where detergent can remain. If the vehicle is particularly dirty, the certified service technician will wash it twice. The first washing will remove the majority of the dirt, and the second will remove any remaining dirt from the vehicle.

The certified service technician then proceeds to clean the vehicle and/or structure's glass. In the preferred embodiment, the glass is cleaned with a composition containing ammonia. A first embodiment of the composition may comprise: approximately 33% white vinegar and 67% water. A second embodiment of the composition may comprise: 0.5 cup of ammonia, 1 pint 70% isopropyl alcohol, 1 tablespoon dish washing detergent, and 1 gallon water. A third embodiment of the composition may comprise plain water, distilled water, or collected rainwater. The certified service technician then proceeds to clean the interior surfaces of the vehicle and/or structure. The certified service technician cleans the interior surfaces with an industrial cleaning composition. The certified service technician drenches a cloth in the industrial cleaning composition and then applies it liberally to an interior surface section of about 1'×2' or less. The certified service technician quickly follows up by wiping down the section with a micro fiber towel. In some cases the certified service technician may utilize a rotary machine for cleaning the vehicle and/or structure's interior surface, carpet cleaners, and leather cleaners too.

Leather requires essential oils to keep its luster. The certified service technician starts with the leather cleaner and works it in gently with minimal water on an applicator. After applying the leather cleaner, the certified service technician rinses the applicator and wipes it down again. Once wiped down, the section is towel dried. The same procedure may be utilized to apply a leather conditioner. In the preferred embodiment, several applications of conditioner, as opposed to one heavy one, is desired if the leather needs it.

The certified service technician then dips a cotton swab within the industrial cleaning composition and places it into vents of the vehicle and/or structure's air-conditioning system. The certified service technician then uses an unused cotton swab for drying the vents.

In the case of vehicles, the certified service technician then cleans the dash, buttons, crevices and bezels. In the preferred embodiment, the certified service technician removes dust and dirt from these areas by using small cans of compressed air. Cotton swabs also work well here. Glass or plastic gauge lenses are cleaned with a glass or plastic cleaner, not wax. The certified service technician pulls off any removable knobs to clean the bezels underneath.

If the carpets are clean except for minor stains, the certified service technician uses a foaming cleaner to get them out. The stain is saturated with the foaming cleaner, working it in with a damp sponge. After a first predetermined time period, the stained area is dried with paper towels or a dry cotton cloth. This step may be repeated if necessary without oversaturating the stained area and risking mildew.

In step B) of the method, vacuuming said vehicle and/or structure with a vacuum having a hepa filter; the hepa filter is defined as a high efficiency particulate air filter by the United States Department of Energy. This type of air filter can theoretically remove at least 99.97% of dust, pollen, mould, bacteria and any airborne particles with a size of 0.3 micrometers ($\mu$m) at 85 liters per minute (L/min). The diameter specification of 0.3 $\mu$m responds to the worst case; the most penetrating particle size ("MPPS"). Particles that are larger or smaller are trapped with even higher efficiency. Using the worst-case particle size results in the worst-case efficiency rating (i.e. 99.97% or better for all particle sizes).

The certified service technician uses a strong vacuum having a predetermined suction power. Unapproved vacuums include, but are not limited to, small ones that plug into a cigar lighter or operate on rechargeable batteries that just don't have the power to adequately collect matter deposited onto the vehicle and/or structure's surface. The certified service technician uses a brush attachment for surface areas that can be marred with an impact from a hard-edged vacuum attachment.

In step C) of the method, placing protective gear on a technician; the protective gear comprises gloves, eye protection comprising polarized goggles, and a N-95 mask for protection. In the preferred embodiment, latex gloves are provided for the certified service technician. As determined by The National Institute for Occupational Safety and Health ("NIOSH"), the N-95 mask comprises a particulate filter, having a 95% efficiency level, effective against particulate aerosols free of oil and all particulate aerosols wherein time use restrictions may apply.

In step D) of the method, opening windows of said vehicle and/or structure; the vehicle and/or structure windows may be lowered entirely and at least half way.

In step E) of the method, reducing and/or eliminating all illumination means; reducing and/or eliminating light is required to clearly detect matter deemed troubled and/or organic.

In step F) of the method, determining and noting vehicle and/or structure identification number of said vehicle and/or structure; the certified service technician notes it.

In step G) of the method, inspecting interior of said vehicle and/or structure with a high intensity long wave ultraviolet light of at least 300 nm; the ultraviolet light ionizes oxygen to produce ozone and can kill many surface pathogens. The high intensity long wave ultraviolet light is positioned at a first predetermined distance from the vehicle and/or structure surfaces. In the preferred embodiment, the first predetermined distance is six to eight inches and the high intensity long wave ultraviolet light is in the range of 345 nm and 385 nm, and preferable 365 nm. In step H) of the method, identifying location of troubled and organic matter; the certified service technician notes it.

In step I) of the method, noting said location of identified said troubled and organic matter; the certified service technician notes it.

In step J) of the method, engaging air-conditioning system of said vehicle and/or structure; the air-conditioning system is engaged with circulation means to circulate at maximum circulation in the preferred embodiment for the remainder of the process, which is approximately 10-15 minutes.

In step K) of the method, engaging an atomizer; the atomizer reduces a first chemical composition that may be in a liquid form, to a fine spray or mist, for effective application. The first chemical composition is a proprietary EPA registered RTU (ready-to-use) bio-engineered formula.

In step L) of the method, applying a first chemical composition from said atomizer to said vehicle and/or structure; the application of the first chemical composition is best achieved in a fine spray or mist form to maximize reach within the vehicle and/or structure. In operation, the certified service technician uses an atomizer nozzle at a second predetermined distance of approximately 8-12 inches from the vehicle and/or structure's surface for a period of approximately 3-5 seconds to a predetermined level of saturation.

In step M) of the method, inserting wand of said atomizer into vents of said air-conditioning system; the application of the first chemical directly into the vents of the air-conditioning system complements the previous step to maximize reach within the vehicle and/or structure. In the preferred embodiment, the wand is an elongated tube that is sufficiently long and narrow to reach near the air-conditioning system evaporator.

In step N) of the method, disengaging said atomizer; the certified service technician disengages it.

In step O) of the method, applying a second chemical composition to all non-porous surfaces of said vehicle and/or structure; the certified service technician never utilizes the same wipe side to avoid re-depositing of contaminates within the vehicle and/or structure and onto vehicle and/or structure surfaces. In the preferred embodiment, the second chemical composition is sprayed on from a spray bottle from a third predetermined distance of approximately 6-8 inches from the vehicle and/or structure's surface and is left on for a second predetermined time period of approximately 30-90 seconds.

In step P) of the method, wiping said second chemical composition on all non-porous surfaces of said vehicle and/or structure; the certified service technician vigorously wipes down all areas of the vehicle and/or structure including the ceiling if needed. In the preferred embodiment, the certified service technician utilizes a wipe that is folded to a predetermined thickness for maximum saturation without re-using a used wipe side on the vehicle and/or structure surface.

In step Q) of the method, re-inspecting said interior with said high intensity long wave ultraviolet light to identify said troubled and organic matter at said location and going to step K) if said troubled and organic matter is still detected; on the back of a certification card this is an exploded diagram of the vehicle and/or structure before and after for identification marking of the detected troubled and organic matter.

In step R) of the method, certifying in written form that said vehicle and/or structure is decontaminated; the certified service technician certifies it. Certification comprises a written signature by the certified service technician that the procedure was complete and delivered with a before and after report to a customer.

In step S) of the method, placing information in said vehicle and/or structure advising of next certification due; the certified service technician places it.

In step T) of the method, drying said vehicle and/or structure for a predetermined time period; the vehicle and/or structure is left to air dry for approximately 10-15 minutes before allowing customers to take the vehicle and/or structure.

The instant invention proactively combats Sick Car and Sick Building Syndrome, and bacteria, including Pseudomani *aeruginosa, Staphylococcus aureus, Streptococcus pyogenes, Enterobacter aerogenes, Enterococcus (Streptococcus) faecalis*, Vancomycin resistant, *Escherichia coli, Escherichia coli* 0157:H7, *Salmonella choleraesuis*, and *Staphylococcus aureus*.

Furthermore, the instant invention proactively combats viruses, including Herpes Simplex Type2, HIV-1, and Influenza A/Hong Kong Influenza.

Lastly, the instant invention proactively combats fungi, including *Trichophyton mentagrophytes*, and Athlete's foot fungus.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method for sanitizing, comprising the steps of:
    A) cleaning a vehicle and/or structure to be sanitized;
    B) vacuuming said vehicle and/or structure with a vacuum having a hepa filter;
    C) placing protective gear on a technician;
    D) opening windows of said vehicle and/or structure;
    E) reducing and/or eliminating all illumination means;
    F) determining and noting vehicle and/or structure identification number of said vehicle and/or structure;
    G) inspecting interior of said vehicle and/or structure with a high intensity long wave ultraviolet light of at least 300 nm;
    H) identifying location of troubled and organic matter;
    I) noting said location of identified said troubled and organic matter;
    J) engaging air-conditioning system of said vehicle and/or structure;
    K) engaging an atomizer;
    L) applying a first chemical composition from said atomizer to said vehicle and/or structure, application of said first chemical composition is achieved in fine spray or mist form to maximize reach within said vehicle and/or structure, said application discharged from an atomizer nozzle approximately 8-12 inches from said interior surface of said vehicle and/or structure for a period of approximately 3-5 seconds to a predetermined level of saturation;
    M) inserting a wand of said atomizer into vents of said air-conditioning system;
    N) disengaging said atomizer;
    O) applying a second chemical composition to all non-porous surfaces of said vehicle and/or structure;
    P) wiping said second chemical composition on all non-porous surfaces of said vehicle and/or structure;
    Q) re-inspecting said interior with said high intensity long wave ultraviolet light to identify said troubled and organic matter at said location and going to step K) if said troubled and organic matter is still detected;
    R) certifying in written form that said vehicle and/or structure is decontaminated;
    S) placing information in said vehicle and/or structure advising of next certification due; and
    T) drying said vehicle and/or structure for a predetermined time period.

2. The method for sanitizing set forth in claim 1, further characterized in that said vehicle and/or structure includes cars, trucks, RVs, campers, trains, aircraft, floating vessels, and houses, condos, buildings and commercial establishments respectively.

3. The method for sanitizing set forth in claim 1, further characterized in that said cleaning said vehicle and/or structure to be sanitized comprises cleaning glass of said vehicle and/or structure, then cleaning interior of said vehicle and/or structure.

4. The method for sanitizing set forth in claim 1, further characterized in that said hepa filter is a high efficiency particulate air filter that removes at least 90% of dust, pollen, mold, bacteria and any airborne particles with a size of at least 0.3 micrometers (μm), at least 85 liters per minute (L/min), said vacuum having a predetermined suction power to collect dirt and foreign matter.

5. The method for sanitizing set forth in claim 1, further characterized in that said protective gear comprises gloves, eye protection comprising polarized goggles, and a N-95 mask for protection, said N-95 mask comprises a particulate filter, having at least a 95% efficiency level, effective against particulate aerosols free of oil and all particulate aerosols wherein time use restrictions may apply.

6. The method for sanitizing set forth in claim 1, further characterized in that said windows are opened at least half way.

7. The method for sanitizing set forth in claim 1, further characterized in that said high intensity long wave ultraviolet light is positioned from an interior surface of said vehicle and/or structure approximately six to eight inches to identify said matter deemed troubled and/or organic.

8. The method for sanitizing set forth in claim 1, further characterized in that said air-conditioning system is engaged to maximum circulation for at least 10-15 minutes.

9. The method for sanitizing set forth in claim 1, further characterized in that said atomizer reduces a first chemical composition to a fine spray or mist.

10. The method for sanitizing set forth in claim 1, further characterized in that said wand is an elongated tube that is sufficiently long and narrow to reach an air-conditioning system evaporator.

11. The method for sanitizing set forth in claim 1, further characterized in that said wiping comprises wiping down said vehicle and/or structure ceiling, if needed, without re-using a used wipe side on said interior surface.

12. The method for sanitizing set forth in claim 1, further characterized in that a certification card comprises an exploded diagram of said vehicle and/or structure before and after for identification marking of detected said troubled and/or organic matter.

13. The method for sanitizing set forth in claim 1, further characterized in that said vehicle and/or structure is left to air dry for at least 10-15 minutes.

14. The method for sanitizing set forth in claim 1, for proactively combating Sick Car and Sick Building Syndrome.

15. The method for sanitizing set forth in claim 1, for proactively combating bacteria, including Pseudomani aeruginosa, Staphylococcus aureus, Streptococcus pyogenes, Enterobacter aerogenes, Enterococcus (Streptococcus) faecalis, Vancomycin resistant, Escherichia coli, Escherichia coli 0157:H7, Salmonella choleraesuis, and Staphylococcus aureus.

16. The method for sanitizing set forth in claim 1, for proactively combating viruses, including Herpes Simplex Type2, HIV-1, and Influenza A/Hong Kong Influenza.

17. The method for sanitizing set forth in claim 1, for proactively combating fungi, including Trichophyton mentagrophytes, and Athlete's foot fungus.

18. A method for sanitizing, comprising the steps of:
A) cleaning a vehicle and/or structure to be sanitized;
B) vacuuming said vehicle and/or structure with a vacuum having a hepa filter;
C) placing protective gear on a technician;
D) opening windows of said vehicle and/or structure;
E) reducing and/or eliminating all illumination means;
F) determining and noting vehicle and/or structure identification number of said vehicle and/or structure;
G) inspecting interior of said vehicle and/or structure with a high intensity long wave ultraviolet light of at least 300 nm;
H) identifying location of troubled and organic matter;
I) noting said location of identified said troubled and organic matter;
J) engaging air-conditioning system of said vehicle and/or structure;
K) engaging an atomizer;
L) applying a first chemical composition from said atomizer to said vehicle and/or structure, application of said first chemical composition is achieved in fine spray or mist form to maximize reach within said vehicle and/or structure, said application discharged from an atomizer nozzle approximately 8-12 inches from said interior surface of said vehicle and/or structure for a period of approximately 3-5 seconds to a predetermined level of saturation;
M) inserting a wand of said atomizer into vents of said air-conditioning system;
N) disengaging said atomizer;
O) applying a second chemical composition to all non-porous surfaces of said vehicle and/or structure, said second chemical composition is sprayed on from approximately 6-8 inches from said interior surface of said non-porous surfaces of said vehicle and/or structure and is left on for approximately 30-90 seconds;
P) wiping said second chemical composition on all non-porous surfaces of said vehicle and/or structure;
Q) re-inspecting said interior with said high intensity long wave ultraviolet light to identify said troubled and organic matter at said location and going to step K) if said troubled and organic matter is still detected;
R) certifying in written form that said vehicle and/or structure is decontaminated;
S) placing information in said vehicle and/or structure advising of next certification due; and
T) drying said vehicle and/or structure for a predetermined time period.

* * * * *